United States Patent [19]

Janjua et al.

[11] Patent Number: 5,207,653

[45] Date of Patent: May 4, 1993

[54] SAFETY NEEDLE AND CAP COMBINATION DEVICE

[76] Inventors: Sabiha Janjua, 643 Charlotte St, Sudbury, Ontario, Canada; Danyl M. Stotland, 273 C Craig Henry Drive, Nepean, Ontario, Canada, K2G 4C7

[21] Appl. No.: 768,387

[22] Filed: Sep. 30, 1991

Related U.S. Application Data

[62] Division of Ser. No. 570,154, Aug. 17, 1990, abandoned.

[30] Foreign Application Priority Data

Aug. 18, 1989 [CA] Canada .................................. 608730

[51] Int. Cl.⁵ ................................................ A61M 5/32
[52] U.S. Cl. ..................................... 604/192; 604/263
[58] Field of Search ................. 604/192, 187, 263, 198

[56] References Cited

U.S. PATENT DOCUMENTS

| | | | |
|---|---|---|---|
| 4,539,042 | 12/1985 | Votel | 604/192 |
| 4,573,975 | 3/1986 | Frist et al. | 604/192 |
| 4,643,722 | 2/1987 | Smith, Jr. | 604/192 |
| 4,659,330 | 4/1987 | Nelson et al. | 604/192 |
| 4,717,386 | 1/1988 | Simmons | 604/192 |
| 4,725,267 | 2/1988 | Vaillancourt | 604/192 |
| 4,735,617 | 4/1988 | Nelson et al. | 604/192 |
| 4,735,618 | 4/1988 | Hagen | 604/192 |
| 4,740,204 | 4/1988 | Masters et al. | 604/192 |
| 4,743,233 | 5/1988 | Schneider | 604/192 |
| 4,747,835 | 5/1988 | Sandhaus | 604/192 |
| 4,758,229 | 7/1988 | Doerschner | 604/187 |
| 4,775,367 | 10/1988 | Schmidt | 604/192 |
| 4,944,397 | 7/1990 | Miller | 604/263 X |
| 5,055,102 | 10/1991 | Sitnik | 604/192 |

FOREIGN PATENT DOCUMENTS 915038 11/1972 Canada .
9700 of 1902 United Kingdom .

OTHER PUBLICATIONS

Sumner, "Needlecaps to Prevent Injuries," Infection Control, vol. 6, p. 495, 1985.
Nixon, "Simple Device to Prevent Accidental Needle--Prick Injuries", The Lancet, p. 888, Apr. 19, 1986.
"Twisting Lock Protects Against Used Hypodermic Needles", New Scientist, p. 31, Dec. 10, 1987.
"Health Workers' Fears Spur Changes in Needle Design", Medical World News, p. 57, May 9, 1988.
Goldwater, "Impact of a Recapping Device on Venepuncture-Related Injury", Infect Control Hosp. Epidemiol vol. 10, p. 21, 1989.

Primary Examiner—John D. Yasko
Attorney, Agent, or Firm—Elman & Wilf

[57] ABSTRACT

A safety needle and cap combination is disclosed which significantly reduces the chances of a needlestick injury when recapping the needle. The cap is pivotally attached to the needle hub, and has a longitudinal slit to accomodate the needle. In an alternative embodiment of the invention, the cap cannot be pivoted open until the needle cap is slid out along a guide to a detent position. Closure can be done with one hand, well away from the needle point, by pressure against a convenient surface.

16 Claims, 3 Drawing Sheets

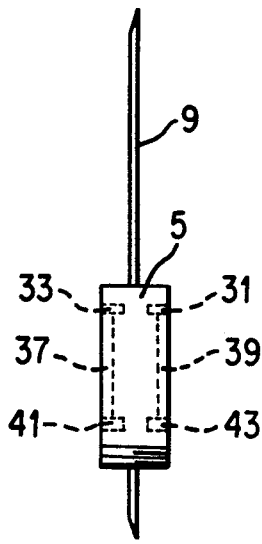
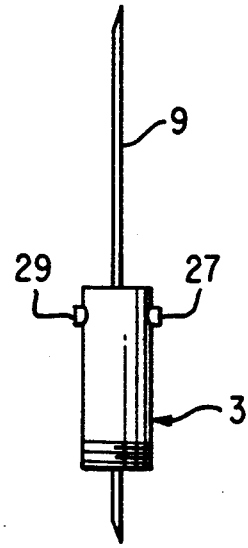
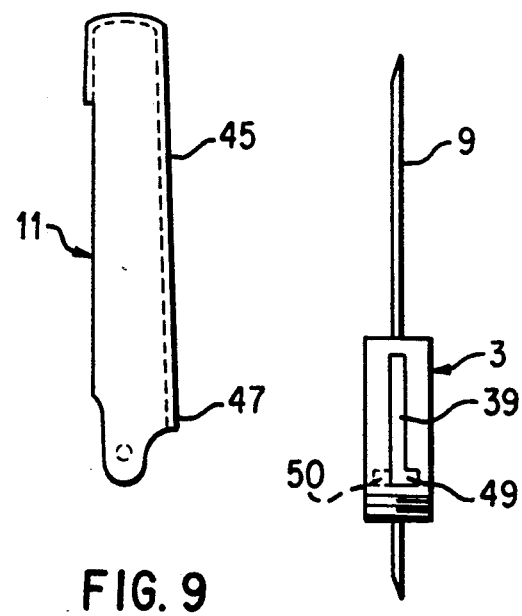
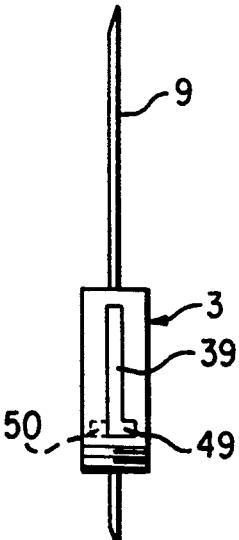
FIG. 7  FIG. 8  FIG. 9  FIG. 10
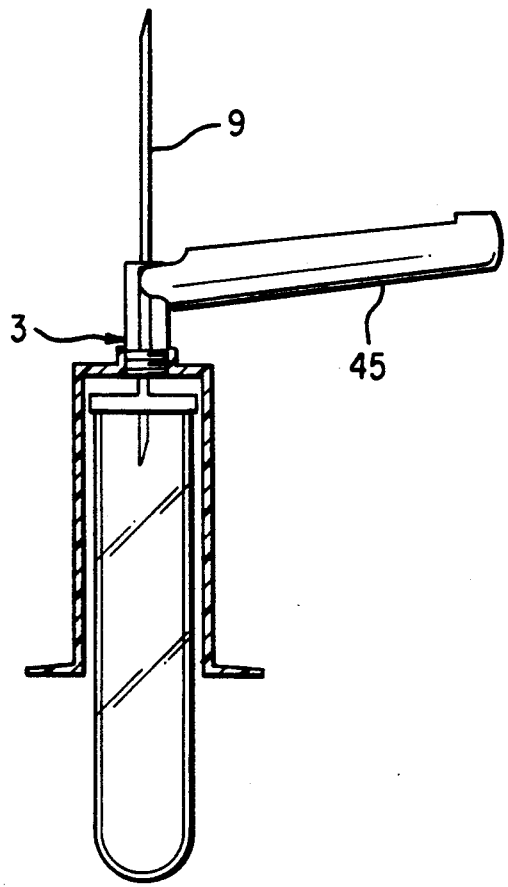
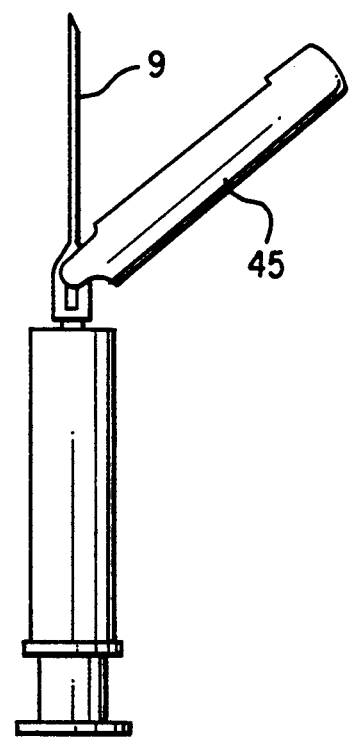
FIG. 11  FIG. 12

SAFETY NEEDLE AND CAP COMBINATION DEVICE

This is a divisional application Ser. No. 07/570,154, filed on Aug. 17, 1990, now abandoned.

BACKGROUND OF THE INVENTION

Needles have been used in medicine since at least as early as 1853, when Alexander Wood used one to administer morphine to a patient. Needle use is now ubiquitous. They are used for, among other duties, removal of blood and other fluids from patients, injections of medication and intravenous administration of fluids. The benefits of hypodermic needles to medicine are many, but there are some problems.

Needlestick injuries are very common. There were about 800,000 needlestick injuries in the Unites States in 1986 alone. Nurses, nurses' aides, phlebotomy technicians and doctors are subject to these injuries. They suffer needle stick injuries when removing blood-slippery needles from syringes or, more commonly, when recapping used needles. The latter mishap occurs when the health professional misses the small target that is the cap's opening, and stabs the hand or finger that holds the cap. Unsheathed needles are sometimes accidentally placed in pockets, which can cause hip injuries.

30% of needlestick injuries happen to the above-mentioned health professionals. The other 70% occur in the chain of disposal. Uncapped needles often end up in plastic disposal bags. Those needles can puncture the bag and anyone who is in close contact with that bag.

Needlestick injuries are potentially very serious. Many blood-borne diseases may be transmitted from the patient to the health professional by inoculation through a needlestick injury. These include diseases such as syphilis, tuberculosis, malaria, herpes and, most ominously, hepatitis B and non-A non-B hepatitis. There is a 26% chance of contracting hepatitis B from any needlestick injury. *Type B Hepatitis after Needle-Stick Exposure* . . . L. B. Seeff et al., Ann. Intern. Med, 1978, 88; 285-293.

Though rare, Acquired Immune Deficiency Syndrome (AIDS) has been transmitted through needlestick injuries. Such a case was reported in *HIV Seroconversion After Needlestick*, in New England J. Med., Aug. 28, 1986, p.582.

The U.S. Occupational Health and Safety Administration has adopted guidelines from the Center for Disease Control, Atlanta, in advising all health professionals not to recap needles. However, most health care workers still recap needles, for a variety of reasons. Some are bound by habits learned in the era before disposable needles and AIDS, others because they perceive the risk of injury from carrying an uncapped needle to a disposal bin is greater than the risk of recapping.

Numerous patents have been granted for devices to prevent needlestick injuries. U.S. Pat. Nos. 4,539,042 and 4,573,975 disclose shields that surround the needle cap. U.S. Pat. No. 4,717,386 discloses a wide paddle-like device which grips the needle cap in its center.

U.S. Pat. No. 4,758,229 dispenses with needle recapping. Needles are placed on an adhesive pad which is then folded over to bury the needle, prior to disposal of the sandwich.

Retractable cover devices are disclosed in U.S. Pat. Nos. 4,659,330; 4,743,233; 4,735,618 and 4,725,267. After use the cover means is pushed up from its resting position, on the needle hub of the syringe barrel, to cover the needle.

The preceding patents require special extra attachments, with their attendant extra cost.

Canadian patent 915,038 does not use any extra fittings. It discloses a needle cap that attached to the needle hub. The cap has a slit which can accommodate the needle cannula. The slit width is less than the needle width, but the cannula can be forced into the cap's slit and be retained. Closure requires both hands, and there is some risk of needlestick.

Other devices have been invented that allow for disposal of uncapped used needles. Plastic disposal devices or containers are provided in many hospital rooms. The containers are impenetrable to needles. Such sharps buckets should be situated in every hospital room and area. That is the ideal, which is rarely achieved. The buckets fill up quickly, and users may be injured by needles protruding from full buckets when attempting to dispose of an additional needle. Needle users must journey to the sharps bucket which is often in another room, in order to dispose of an uncapped needle Phlebotomy technicians take many blood specimens, and are more apt to recap a needle than to continually return to a needle receptacle in order to discard the uncapped used needle.

The present invention provides for a needle and cap combination which allows for capping of the used needle with the use of one hand only. During capping, that hand does not come near the needle's point. Closure requires pushing the side of the cap against a convenient surface to pivot the cap and thus cover the needle. In another embodiment, a further push locks the cap, preventing subsequent accidental uncovering of the needle through pivotal action. In a further embodiment, an additional twist can further secure the cap covering the needle, to make accidental uncovering of the needle almost impossible. A further embodiment discloses a method to modify the needle, to render it subsequently unusable

BRIEF DESCRIPTION OF THE DRAWINGS

These embodiments of the invention will now be described in detail with the aid of the accompanying drawings wherein

FIG. 7 is a schematic representation of a needle and hub as in FIG. 6, but with two detent positions.

FIG. 8 is a schematic representation of a needle and hub featuring the pivot points on the hub.

FIG. 9 is a schematic representation of a needle cap showing a modification which allows pivoting to only one side.

FIG. 10 is a schematic representation of a needle and hub featuring a twist modification that allows a corresponding needle cap to be secured in an open or closed position.

FIG. 11 is a schematic representation of a needle and hub, and a longitudinal section of a vacuum collection system, showing their attachment with the needle cap in an opened position.

FIG. 12 is a schematic representation of needle and hub of the invention, adapted to fit on a syringe, through a luer friction fit.

DESCRIPTION OF EMBODIMENTS OF THE INVENTION

Figure 1:
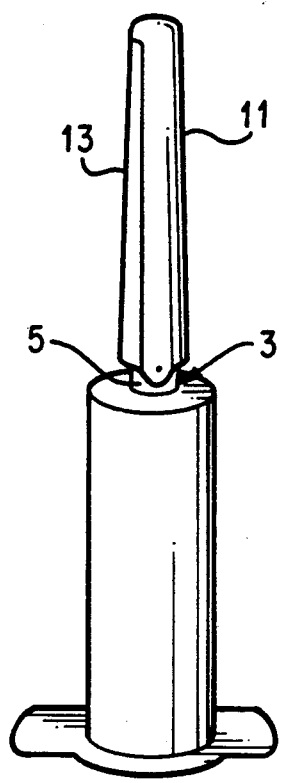
FIG. 1 is an elevation of one embodiment of the invention, mounted on the tube holder portion of a vacuum phlebotomy device.
Figure 2:
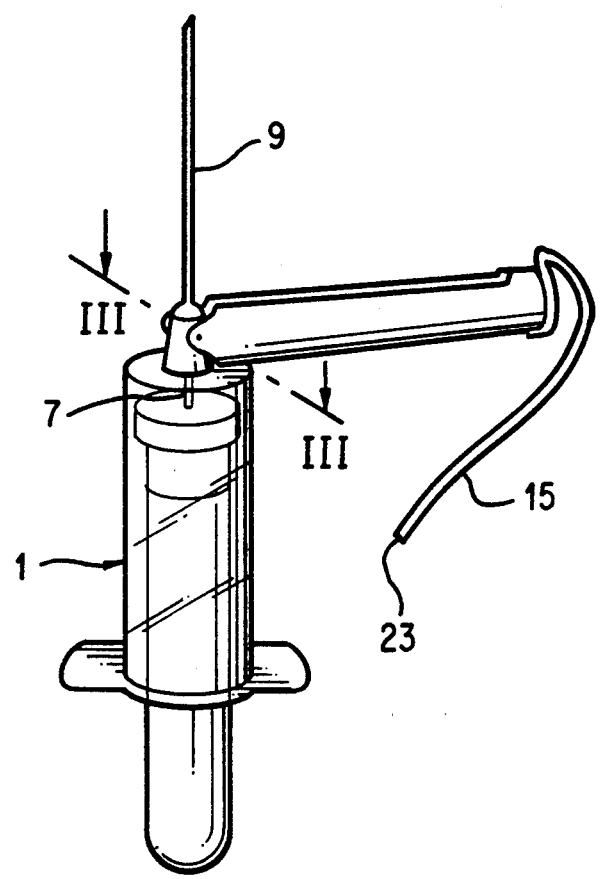
FIG. 2 is a depiction of the device of FIG. 1, mounted on a vacuum phlebotomy device, with the needle cap pulled open.
Figure 3:
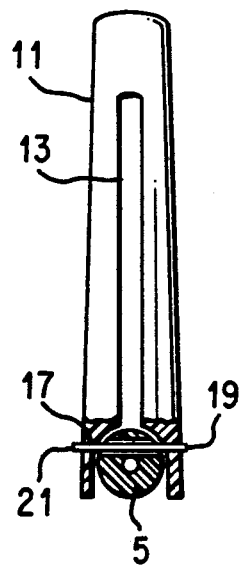
FIG. 3 is a plan view schematic cross section of the line III—III of FIG. 2.

The invention in its simplest embodiment is illustrated in FIGS. 1 to 3. FIG. 2 shows a fluid collecting vessel, in this particular depiction a vacuum collection vessel 1 sometimes known as a Vacutainer[1], and a double needle and hub piece 3 comprised of hub 5 with small needle 7 on one end and larger sampling needle 9 on the other end. Part of hub 5 and all of larger sampling needle 9 can be covered by needle cap 11.

[1] Denotes trademark.

Needle cap 11 has a longitudinal slit 13 of a width greater than the diameter of larger needle 9, in order to accommodate it, and hub clearance notch 25 adapted to clear the top of hub 5. Slit 13 can be covered by cover piece 15, shown peeled off in FIG. 2 Cover piece strip 15 may be made of a strip with an adhesive on the needle cap contacting side.

Needle cap 11 is adapted to be pivotally connected with needle and hub piece 3, by pivotal connecting means. The specific pivotal connecting means of the embodiment depicted in FIGS. 1, 2 and 3 is a pivot pin 17 seen in FIG. 3. Pivot pin 17 is situated in hub 5 with protruding ends 19 and 21 situated on both ends. Protruding ends 19 and 21 each respectively fit in needle cap 11. Needle cap 11 is adapted to pivotally move about protruding ends 19 and 21 of pivot pin 17

Needle cap 11 and hub piece of needle and hub portion 3 may be made of plastic and are usually one-use disposable items.

In operation, needle and hub piece 3 is threaded to vacuum collection vessel 1. Strip 15 of needle cap 11 is peeled back. Needle cap 11 is pulled back. Longitudinal slit 13 clears sampling needle 9 and hub clearance notch 25 clears hub 5 when needle cap 11 pivots on protruding ends 19 and 21 of pivot pin 17. Sampling is done through sampling needle 9. Fluid is drawn into vacuum collection vessel 1 by vacuum. The phlebotomist may cover the needle by grasping vacuum collection vessel 1 with one hand, and contacting the side of needle cap 11 with a convenient surface such as a wall or table top. Pressure will cause needle cap 11 to pivot and cover sampling needle 9. The phlebotomist may, optionally, cover longitudinal slit 13 by grasping end 23 of cover piece strip 15 with the other hand, and taping longitudinal slit 13 shut.

This embodiment may be used for a syringe and needle combination, as depicted in FIG. 12.

FIGS. 4 through 14 depict other embodiments of pivotally connecting needle and hub piece 3 with needle cap 11.

Figure 4:
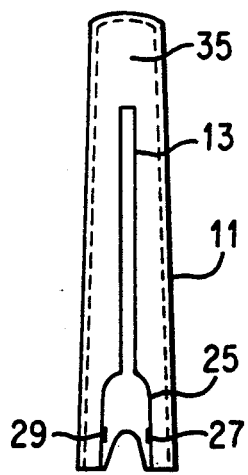
FIG. 4 is a schematic representation of a needle cap, showing another embodiment of the invention.

FIG. 4 shows a needle cap 11, with longitudinal slit 13, hub clearance notch 25 and pivot protrusions 27 and 29. Pivot protrusions 27 and 29 are adapted to pivot in depression 31 and 33 respectively of needle and hub piece 3 of FIG. 3.

Operation is similar to that of the device of FIGS. 1, 2 and 3, with pivotal protrusions 27 and 29 pivoting in depression detents 31 and 33 respectively.

Figures 5, 6:
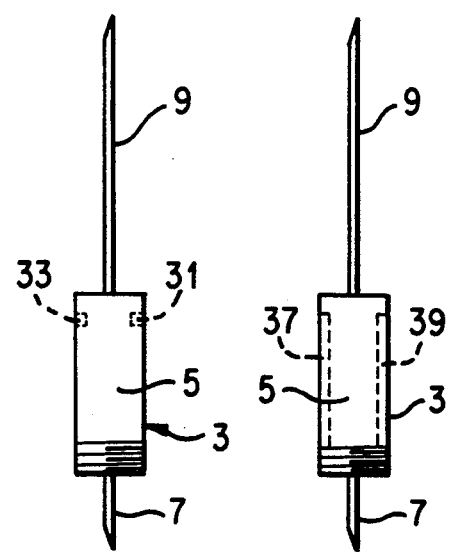
FIG. 5 is a schematic representation of a needle and hub adapted to receive the needle cap of FIG. 4.
FIG. 6 is a schematic representation of a needle and hub adapted to slidably receive the needle cap of FIG. 4.
Figure 13:
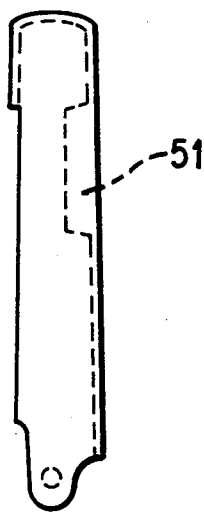
FIG. 13 is a schematic representation of a needle cap, as in FIG. 9, showing a guidance piece which facilitates its slidable registration with a corresponding needle and hub of the invention.

FIGS. 6 and 7 depict a preferred embodiment of the invention. The needle and hub piece 3 has slots 37 and 39. The embodiment of FIG. 7 has depression detent positions 41 and 43, and 31 and 33. Slot 37 and 39 are adapted to receive pivot protrusions 29 and 27 respectively of the needle cap 11 of FIGS. 4, 9, 11, 13, 14, 15 or 16.

Figure 14:
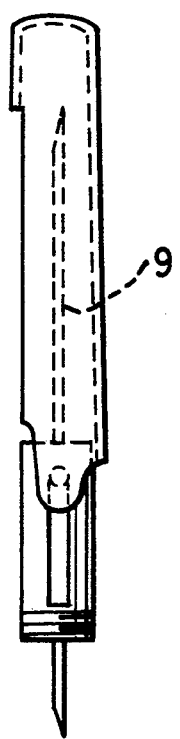
FIG. 14 is a schematic representation of the needle cap of FIG. 9 and a corresponding hub and needle, showing registration of pivot points and needle cap sliding slot.

In operation, as depicted in FIGS. 11 and 14, pivot protrusions 29 and 27 rest in proximal depression detents 43 and 41. In this position, sampling needle 9 is safely located in needle cap 11 with shield section 35 of FIG. 4 preventing outward pivotal movements of needle 9 from needle cap Needle cap 11 is grasped and pulled outward from hub 5. Pivot protrusions 29 and 27 slide along slots 37 and 39, until they reach depression detents 33 and 31. The transition between the detents and slots may be sloped for greater ease of movement, instead of the abrupt discontinuity shown in FIG. 7. In this position, needle cap 11 may be pivoted to the open position seen in FIG. 11. Sampling needle 9 is no longer obstructed by shield section 35 of needle cap 11, and it passes through longitudinal slit 13 and, simultanously, the hub clearance notch 25 clears the top portion of hub 5.

The pivoting motion is done by pivot protrusions 29 and 27 rotating in depression detents 33 and 31 respectively.

After needle use, sampling needle 9 may be safely secured in needle cap 11. This is accomplished by pushing back portion 45 of needle cap 11 against a convenient surface, until basal back portion 47 of needle cap II contacts hub 5. After the contact is made, the needle cap 11 is pushed in toward hub 5 by pushing end 49 against a convenient surface. This pushing causes pivot protrusions 27 and 29 to slide in slots 39 and 37 in the direction of hub 5. The motion of needle cap 11 ends when protrusions 27 and 29 reach proximal depression detents 41 and 43. The effect is that sampling needle 9 cannot now be pivoted out of needle cap 11, as its tip is prevented from movement by cap shield section 35.

These two pushing motions may be done with only one hand, which grasps vacuum collection vessel 1. The hand is well away from the tip of sampling needle 9. If desired, cover piece strip 15 may be applied to cover longitudinal slit 13.

In another embodiment of the invention, seen in FIG. 8, pivot protrusions 27 and 29 are mounted on the needle and hub piece 3, and corresponding slots may be place in the inside of needle cap 11, not shown.

The function of the device of the embodiment of FIG. 8 is essentially similar to that of FIGS. 4, 6 and 7.

The embodiment of FIG. 10 features a locking system to prevent accidental travel of the needle cap 11 on the needle and hub piece 3 which could allow sampling needle 9 to pivot out of needle cap 11.

Needle and hub piece 3 of FIG. 10 features two lateral channels 49 and 50, at the base of each slot and in communication therewith. The lateral channels are disposed on opposite sides of the plane defined by slots 37 and 39.

It is important that needle cap pivot protrusions 27 and 29 align with slots 37 and 39 when pivoted closed in order to push the needle cap 11 toward hub 5. As discussed above, basal back portion 47 contacts hub 5 to effect alignment.

Figure 15:
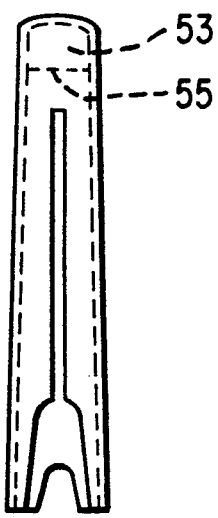
FIG. 15 is a schematic representation of another embodiment of the invention, featuring a compartment in the end of the needle cap, capable of storing glue or lubricant.

In a further alternate embodiment, depicted in FIG. 15, the anterior distal end portion of needle cap 11 may be adapted to contain a pocket 53 with closure membrane 55, which may contain desirable chemicals. For example, it may contain silicone or cyanoacrylate glue to plug sampling needle 9 after use. Alternatively, pocket 53 may contain a disinfectant gel.

Figure 16:
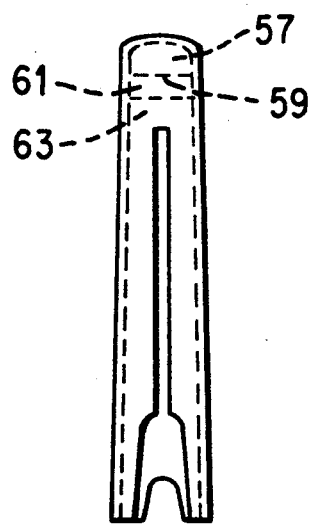
FIG. 16 is a schematic representation of a needle cap similar to that of FIG. 15 featuring two adjacent compartments.

In a further alternate embodiment depicted in FIG. 16, there is a double pocket with two compartments 57 and 59 with pocket partition 59 and closure membrane 63. Epoxy resin and hardener may fill adjacent pockets, respectively.

Figure 17:
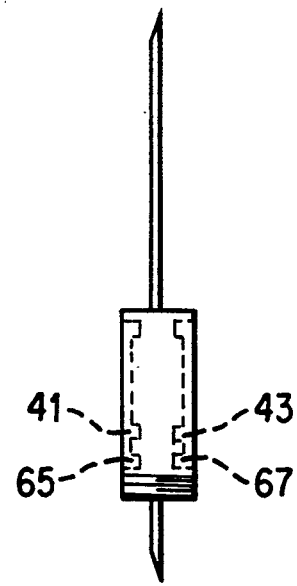
FIG. 17 is a schematic representation of a needle and hub, featuring three detent positions, adapted to operate with the needle caps of FIGS. 15 and 16.

The pockets of FIGS. 15 and 16 may be pierced by a sampling needle 9 of the embodiment of FIG. 17. The needle and hub piece 3 has an extra set of detents 65 and 67, located below proximal depression detents 41 and 43. The extra set of detents are located on extended slots 37 and 39.

In use, needle cap 11 is pivoted shut, pushed down and the hub 5, and then further pushed beyond proximal depression detents 41 and 43 to a position wherein pivot protrusions 27 and 29 reach the bottom of travel in slots 39 and 37 respectively. This would correspond to detent positions 67 and 65 in FIG. 17. Detents are not absolutely necessary. In so doing, sampling needle 9 pierces one pocket 53 in the device of FIG. 15, or two pockets 59 and 57 in the device of FIG. 16. Sampling needle 9 has the top of its bore filled with the contents of the pockets. Needle reuse would be prevented.

Specific embodiments of the invention have been described in the disclosure. It will be evident to those skilled in the are that numerous variations of the details may be made without departing from the invention as defined in the claims.

The embodiments of the invention in which an exclusive property or privilege is claimed are defined as follows:

1. A safety needle and closure cap device consisting essentially of in combination
   (i) a hub including a substantially axial flow channel;
   (ii) a needle attached to the hub and in fluid flow communication with the channel;
   (iii) a needle cap closure moveable by rotation between a first closed position covering the needle and a second open position exposing the needle; and
   (iv) pivot means comprising two pivot protrusions and two cooperating sots, whereby the cap is slidably attached to the hub, moving from a first safety position to a second pivot position, and having an axis of rotation substantially perpendicular to the axis of the needle;

wherein the needle cap includes a longitudinal slit on one side thereof through which the needle passes on rotation of the cap either from the first closed position to the second open position, or from the second open position to the first closed position.

2. A device according to claim 1 wherein the protrusions are incorporated into the hub and the slots are incorporated into the cap.

3. A device according to claim 1 wherein the slots are incorporated into the hub and the protrusions are incorporated into the cap.

4. A device according to claim 3 wherein the slidable connection means further includes a radial rotation means, permitting twisting of the cap in the first position.

5. A device according to claim 4 wherein the slidable connection means includes a radial rotation means comprising two pivot protrusions, and two cooperating slots each including a longitudinal portion and a short radial portion.

6. A device according to claim 3 wherein the slidable connection means further includes a radial rotation means, permitting twisting of the cap in the first position, and wherein the protrusions are incorporated into the cap and the slots are incorporated into the hub.

7. A device according to claim 1 wherein said cap has a guide stop substantially opposite to said longitudinal slit, said guide stop being adapted to contact said needle upon closure of said cap.

8. A device according to claim 1 wherein said cap is elongate and has disposed therein at its closed end a closed pocket, said cap being adapted to slide a closed position beyond the normal rest position, wherein said needle pierces said pocket.

9. A device according to claim 1 wherein said cap is elongate and has disposed therein at its closed end a closed pocket, said cap being adapted to slide to a closed position beyond the normal rest position, wherein said needle pierces said pocket.

10. A device according to claim 8 wherein said pocket is adapted to contain material from the group comprising disinfectants, material that can plug the needle lumen, or glue.

11. A device according to claim 8 wherein said closed pocket is comprised of two adjacent compartments.

12. A device according to claim 11 wherein one of said compartments is adapted to contain epoxy resin and the other of said compartments is adapted to contain an epoxy hardening catalyst.

13. A device according to claim 8 wherein said hub has two pairs of parallel slots wherein the bottom end of one set are in communication with the top of the other set of lateral channels, the combination being adapted to prevent accidental closure and piercing of the pocket by said needle.

14. A device according to claim 1 wherein said needle cap closure further comprises a shield section.

15. A device according to claim 14 wherein said slots have at least one depression located at the pivot position distal to said hub, said pivot depression being adapted to stop the travel of the cap in said slot and to allow rotation of the cap to expose the needle.

16. A device according to claim 15 wherein said slots have at least one depression located at the safety position proximal to said hub, whereby when said needle cap closure is located in the safety position, said safety depression prevents accidental movement of the needle cap closure to said pivot position and said shield section prevents accidental rotation of said needle cap closure from the first closed position to the second open position.

* * * * *

UNITED STATES PATENT AND TRADEMARK OFFICE
CERTIFICATE OF CORRECTION

PATENT NO. : 5,207,653
DATED : May 4, 1993
INVENTOR(S) : Janjua et al.

It is certified that error appears in the above-identified patent and that said Letters Patent is hereby corrected as shown below:

Column 1, line 44 "needles-tick" should read -- needlestick --.
Column 2, line 23 "needle Phle-" should read --needle. Phle- --;
  line 49 "unusable" should read --unusable.--.
Column 3, line 45 "FIG. 2" should read --FIG. 2.__;
  line 56 "pin 17" should read --pin 17.--.
Column 4, line 34 "from needle cap" should read --from needle cap 11.--.
Column 5, line 37 "and the hub" should read -- toward the hub --.

line 64 "sots" should read --slots--.

Signed and Sealed this

First Day of February, 1994

Attest:

BRUCE LEHMAN

*Attesting Officer*  *Commissioner of Patents and Trademarks*